United States Patent [19]

Hamann et al.

[11] Patent Number: 5,254,271
[45] Date of Patent: Oct. 19, 1993

[54] AMMONIUM COMPOUNDS, PREPARATION THEREOF AND USE THEREOF AS CLEANING AGENT, COSMETIC RAW MATERIAL AND SOFTENER, IN PARTICULAR AS FINAL-RINSE FABRIC SOFTNER

[75] Inventors: Ingo Hamann, Bad Orb; Elke Hohn; Hans-Jurgen Kohle, both of Schuchtern; Winfried Wehner, Neuhof; Joachim Weigand, Freigericht, all of Fed. Rep. of Germany

[73] Assignee: Rewo Chemische Werke GmbH, Fed. Rep. of Germany

[21] Appl. No.: 861,451

[22] Filed: Apr. 1, 1992

[30] Foreign Application Priority Data

Apr. 3, 1991 [DE] Fed. Rep. of Germany ....... 4110663

[51] Int. Cl.$^5$ ................... D06M 10/08; C11D 17/00; C11D 1/12; A61K 7/06
[52] U.S. Cl. .................................... 252/8.8; 252/8.9; 252/174; 252/542; 252/554; 424/70
[58] Field of Search ................. 252/8.8, 8.6, 8.7, 8.75, 252/8.9, 542, 554, 174; 424/70

[56] References Cited

U.S. PATENT DOCUMENTS

| | | | |
|---|---|---|---|
| 2,482,761 | 9/1949 | Goebel | 260/407 |
| 2,875,218 | 2/1959 | Dazzi | 260/404.5 |
| 3,256,304 | 6/1966 | Fischer et al. | 260/407 |
| 3,328,409 | 6/1967 | Wakeman et al. | 260/286 |
| 3,763,053 | 10/1973 | Bills | 252/357 |

FOREIGN PATENT DOCUMENTS

| | | | |
|---|---|---|---|
| 1109753 | 9/1981 | Canada | 252/8.8 |
| 4831958 | 10/1973 | Japan | 252/8.8 |
| 1601815 | 11/1981 | United Kingdom . | |

*Primary Examiner*—Paul Lieberman
*Assistant Examiner*—William S. Parks
*Attorney, Agent, or Firm*—Scully, Scott, Murphy & Presser

[57] ABSTRACT

Ammonium compounds and the use thereof as fabric softener comprising mixtures of quaternary ammonium compounds with or without ester groups prepared by reacting amines with dimerized fatty acids and subsequent quaternization or protonation with inorganic or organic acids.

6 Claims, No Drawings

AMMONIUM COMPOUNDS, PREPARATION THEREOF AND USE THEREOF AS CLEANING AGENT, COSMETIC RAW MATERIAL AND SOFTENER, IN PARTICULAR AS FINAL-RINSE FABRIC SOFTNER

The present invention relates to novel ammonium compounds, processes for preparing them and the use thereof as cleaning agent, cosmetic raw material and softener, in particular as final-rinse fabric softener.

In the washing of textiles it is customary to employ in the last wash cycle fabric softeners in order that harshening of the fabrics by drying may be avoided and the fabric hand of the treated textiles may be positively influenced.

The final-rinse fabric softeners used are customarily cationic compounds, for example quaternary ammonium compounds which in addition to long-chain alkyl radicals may also contain ester or amide groups. It is also advantageous to use mixtures of different softening components which are added to the rinse bath in the form of aqueous dispersions.

These cationic compounds are effective softeners when used in the final-rinse bath, but they do have some disadvantages in use.

One of the disadvantages of such agents is that the softener components are not dispersible in cold water; another is that the textiles treated therewith possess unsatisfactory remoisture capability.

Remoisture capability for the purposes of the present invention is the ability of the fiber to reabsorb moisture. Inadequate remoisture capability is a disadvantage whenever major quantities of moisture are to be absorbed from the surface of the skin, for example in the case of hand and bath towels, underwear and bed linen.

It is an object of the present invention to overcome the abovementioned disadvantages of conventional final-rinse fabric softening formulations and to make available highly concentrated final-rinse fabric softeners which combine ready biodegradability and a soft fabric hand with significantly improved dispersibility or solubility even in cold water and improved remoisture capability.

It has been found, surprisingly, that final-rinse fabric softeners comprising mixtures of quaternary ammonium compounds with or without ester groups that are preparable by quaternization or by protonation with inorganic or organic acids not only meet these requirements but give clear solutions in cold water even in high concentrations of up to about 30% by weight.

The present invention accordingly provides ammonium compounds of the general formula (1)

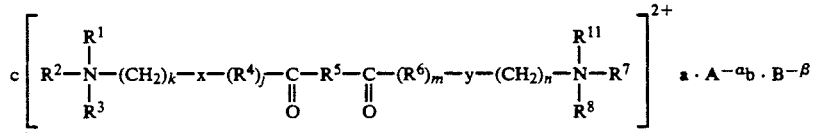

wherein $R^1$ and $R^{11}$ are the same or different and each is H, —CH$_3$, —C$_2$H$_5$, —(C$_3$H$_6$O)$_p$H, or —(C$_2$H$_4$O)$_e$H;

$R^2$, $R^3$, $R^7$ and $R^8$ are the same or different and each is a straight-chain or branched alkyl radical containing 1-18 carbon atoms, or a straight-chain or branched alkylene radical containing 2-18 carbon atoms;

$R^4$ and $R^6$ are the same or different and are represented by the formula —(CH$_2$—CHR$^9$—O)$_d$— wherein d is zero to 20 and in each of the units of the formula —(CH$_2$—CHR$^9$—O)—R$^9$ is independently H or —CH$_3$, provided that $R^9$ is —H in up to 10 of said units and $R^9$ is —CH$_3$ in up to 10 of said units;

$R^5$ is the radical of a dimerized fatty acid;

x and y are independently —O— or —NH—;

$A^{-\alpha}$ and $B^{-\beta}$ are the same or different and each is the anion of a water-soluble monobasic or polybasic inorganic or organic acid, such as methyl-sulfuric acid, ethylsulfuric acid, a halohydric acid, phosphoric acid, formic acid, acetic acid, oxalic acid, glycolic acid, citric acid, tartaric acid, malic acid, and in particular hydrochloric acid and lactic acid, and a, b and c are integers related such that $c = [(a)(\alpha) + (b)(\beta)]/2$;

k and n are the same or different and each is an integer from 2-4;

p and e are the same or different and each is an integer from 1-5; and j and m are the same or different and each is zero or one, provided that j is zero when x is —NH— and m is zero when y is —NH—.

The present invention further provides aqueous final-rinse fabric softeners comprising A) from 5 to 30% by weight of at least one of the compounds of the general formula (1) as defined above;

and to 100% by weight

B) water, dyes, perfume, thickeners and customary auxiliary and additive substances.

According to the invention, preference is given to using compounds of the general formula (1) wherein $R^1$ and $R^{11}$ are the same or different and each is H or —CH$_3$;

$R^2$, $R^3$, $R^7$ and $R^8$ are methyl;

$R^5$ is the radical of a dimerized fatty acid having a dimer content of at least about 80% by weight;

k and n are each 2 or 3;

j and m are zero; and $A^{-\alpha}$ and $B^{-\beta}$ are the same or different and each is the lactate radical or the methylsulfate radical.

The compounds of the general formula (1) used according to the present invention are prepared in a conventional manner, in general by esterifying or amidating the primary/tertiary amine of the formula (2b) shown below, or the alkanolamine of the formula (2a) or (2c) shown below, in the presence of acid catalysts such as methanesulfonic acid or hypophosphorous acid under nitrogen at 140°–200° C. and continuously distilling off the resulting condensate, if necessary under reduced pressure in the final stage. Instead of the dimeric fatty acids it is also possible to use their esters or diesters.

The dimeric fatty acids used for preparing the compounds according to the present invention are the commercially available products which are prepared by polymerization of saturated or unsaturated natural or synthetic monobasic aliphatic fatty acids of 16–22 carbon atoms by known methods (cf. U.S. Pat. Nos. 2,482,761 and 3,256,304). Typical commercially available dimeric fatty acids have approximately the following composition:

| | |
|---|---|
| monomeric acids | 0–15% by weight |
| dimeric acids | 60–95% by weight |
| trimerized acids and higher polymers | 1–35% by weight | the content varying within these limits depending on the origin of the monomers, of the polymerization process and of the workup process.

The dimeric fatty acid used can also be present in hydrogenated form.

The dimeric acid content of the above-described fatty acid composition can be raised to about 100% by weight by generally known distillation methods.

The dimeric acid content is determined by the known methods of gas liquid chromatography (GLC).

If distilled dimeric fatty acid is used, the products obtained have an improved color number. On the other hand, it is perfectly possible to use commercial technical-grade polymerized fatty acid for the preparation. If technical-grade dimeric fatty acid is used, it should be pointed out that relatively high trimeric fatty acid contents may result in products having a poorer color number and higher viscosities. This depends on the particular level of dimeric and monomeric fatty acid in the polymerized fatty acid, and the desired values can be determined in a few simple exploratory experiments of the kind which are within the capability of a person of average skill in the art to which this invention relates. If desired, it is also possible according to the invention to use the distillation residues from the distillation of the dimerized fatty acids alone or mixed with commercially available dimeric fatty acids. These distillation residues generally have approximately the following composition:

| | |
|---|---|
| monomeric acids: | 0–1% by weight |
| dimeric acids: | 15–25% by weight |
| trimeric and higher polymeric acids: | 75–85% by weight |

However, preference is given to distilled dimeric fatty acid having a dimeric fatty acid content of 80–96%. That is, the dimeric fatty acid intermediate used in synthesis of compounds of the formula (1) has the formula HOOC—$R^5$—COOH formed by the dimerization of fatty acids, which dimerization forms a product which may include monomeric, dimeric, trimeric and higher polymeric acids, wherein in the preferred embodiment the dimeric compounds HOOC—$R^5$—COOH comprise at least about 80% by weight of said product, and at least about 80% by weight of all products of such dimerizations that are present in a composition containing compounds of formula (1).

The alkanolamines or amines with primary and tertiary amine groups in the molecule used according to the present invention are preferably commercially available products of the general formulae (2a) and (2b)

$(R^2)(R^3)N—(CH_2)_{2-4}—OH$ (2a)

$(R^2)(R^3)N—(CH_2)_{2-4}—NH_2$ (2b)

wherein $R^2$ and $R^3$ are each as defined above, but preferably are alkyl radicals of 1–4 carbon atoms each and are more preferably methyl or ethyl radicals.

The compounds of the formula (2a) can be alkoxylated, i.e. preferably—according to the invention—ethoxylated, in a conventional manner. In general this is done by reacting the amine of formula (2a) in a pressure reactor at 120°–160° C., in the presence or absence of basic, in particular alkaline, catalysts, at 1–4 bar with an amount of alkylene oxide, preferably according to the present invention ethylene oxide and propylene oxide or mixtures thereof, corresponding to the desired degree of alkoxylation.

The products obtained are compounds of the general formula (2c)

$(R^2)(R^3)N—(CH_2)_{2-4}—O—(CH_2CHR^9—O)_dH$ (2c)

wherein d indicates that there are up to 20 repeating units of the formula —$CH_2CH(R^9)O$—. In each of those units, $R^9$ is independently —H or —$CH_3$, depending on the reactants; there are up to 10 units in which $R^9$ is —H and up to 10 units in which $R^9$ is —$CH_3$. The repeating alkoxy units can comprise solely ethoxy, solely propoxy, a random mixture of ethoxy and propoxy, or one or more blocks of polyethoxy and polypropoxy, such as —$(CH_2CH_2O)_{0-10}$—$(CH_2CH(CH_3)O)_{0-10}$.

The compounds used according to the present invention can be protonated with organic or inorganic acids in a conventional manner. This is preferably done by adding the aqueous protonic acid with or without a solvent, for example a short-chain alcohol, to the reaction mixture with intensive stirring.

Examples of the organic acids used are formic acid, acetic acid, methylsulfuric acid, ethylsulfuric acid, in particular lactic acid, malic acid, tartaric acid, citric acid, oxalic acid, glycolic acid; inorganic acids such as halohydric acids, in particular hydrochloric acid, sulfuric acid, phosphoric acid. Preference according to the present invention is given to lactic acid and hydrochloric acid.

Examples of the quaternizing agents used are short-chain dialkyl phosphates and sulfates such as, in particular, dimethyl sulfate, dimethyl carbonate, diethyl sulfate, dimethyl phosphate, diethyl phosphate, and short-chain halohydrocarbons, in particular methyl chloride.

The quaternization is effected in a conventional manner. Preference according to the present invention is given to admixing the liquified substance, in the presence or absence of a solvent, preferably a short-chain alcohol such as isopropanol, at 60°–90° C. with equimolar amounts of the quaternizing agent with stirring, under atmospheric or superatmospheric pressure, and following the progress of the reaction by monitoring the total amine number (TOT).

By using the compounds according to the present invention it is possible to prepare final-rinse fabric softeners which give clear solutions even in cold water in concentrations of up to about 25–30% by weight, based on total mixture, and confer on textile materials, in particular those made of natural and regenerated cellulose and also wool and terry, not only a soft fabric hand but also excellent remoisture capability.

The final-rinse fabric softeners according to the present invention are therefore used not only on the usual textile materials but in particular wherever large amounts of wetness and moisture are to be removed from the body surface within a short time, such as on hand and bath towels. But the final-rinse fabric softeners according to the present invention are also successfully usable where moisture has to be absorbed directly from the skin within longer time spans, such as on underwear or bed linen.

The final-rinse fabric softener concentrates are prepared by dissolving the particular individual components in water. This can be done using the procedures for dispersions customary in this field, but there is no need for the otherwise necessary heating of the water or the active ingredient.

The customary procedure for doing this comprises adding with thorough stirring to the initially charged water at room temperature first the dye solution, then the antifoam emulsion which may be necessary and then the active ingredient of formula (1) according to the present invention. If necessary, or desired, customary auxiliary and additive substances and perfume oils can likewise be added. They are in particular complexing agents, optical brighteners, dyes, scents, electrolytes and higher molecular weight ether compounds for viscosity regulation, small amounts of organic solvents and—provided they have no adverse effect on the remoisture capability—customary surfactants. If necessary the pH is adjusted to about 3-5 with the inorganic or organic acids customary in this field, in particular HCl, $H_3PO_4$, $H_2SO_4$, lactic acid or citric acid.

Like the prior art fabric softeners, the fabric softeners according to the present invention are added to the final-rinse cycle immediately following the actual washing process. The concentration after dilution with water varies with the field of application within the range from 0.1 to 10 g of fabric softener per liter of treatment liquor.

The concentrates obtained with an active ingredient content of up to about 30% by weight, based on the total formulation, are clear solutions of low viscosity which, in addition to having the abovementioned advantages, are markedly easy to disperse in the rinse water of the washing machines.

To assess the fabric hand, the textile material, made of wool, cotton, 50:3 polyester/cotton and polyester, is treated for about 10 minutes with a liquor comprising tap water (about 9° German hardness and a temperature of 15°-20° C.) and the novel dispersion. The concentration of the compounds according to the present invention in the liquor is 0.025% by weight, based on the total active ingredient. The dried textiles were checked by nine people with experience in the assessment of the softness of textiles in respect of their soft fabric hand and assessed against textiles which had either not been treated with fabric softeners or which had been treated with a commercially available fabric softener. The assessments are rated according to a graduated points system, the final reported result being the arithmetic average. After drying, the textile material thus treated has an excellent soft fluffy fabric hand, and compared with commercially available agents, a much improved remoisture capability.

The remoisture capability is measured on the lines of German Standard Specification DIN 53 924, except that the strips of fabric (test pieces) are 1.5 cm in width.

Aside from their use in final-rinse fabric softeners the compounds according to the present invention can be used with success in hair and body care agents, in household and industrial cleaning agents and also in textile auxiliaries, in particular as softener/hand finish with hydrophilizing properties and high substantivity for the final finish of textiles.

In the examples which follow, the abbreviations used have the following meaning:
AN = acid number
TOT = total amine number
TERT = tertiary amine number
Cat. $SO_3$ = cationic substance.

These analytical values are determined by the following methods generally customary in this field:

Acid Number (AN)

The acid number is a measure of the free acid content of a fat or technical-grade fatty acid and indicates the milligrams of potassium hydroxide which are necessary for neutralizing 1 gram of substance.

The values are determined by DGF (German Society for Fat Chemistry) standard method C-V4.

Cationics Content (Cat. $SO_3$)

This method is used for determining the level of cationic substances. Here the cationic substances are long-chain compounds which contain quaternary ammonium groups. The content is reported in % of quaternary compound calculated as $SO_3$ equivalent with a molecular weight of 80 g/mol.

It is determined by a two-phase titration as described in ISO standards 2871-1 and 2871-2 (1988 E).

Dry Matter Content

It is determined by heating and drying at 105° C. to constant weight.

Total Amine Number (TOT), Tertiary Amine Number (TERT)

The total amine number indicates the number of milligrams of potassium hydroxide which are equivalent to the total amine basicity of 1 g of the amine compound (mg of KOH/g). The tertiary amine number indicates the number of milligrams of potassium hydroxide which are equivalent to the tertiary amine basicity of 1 g of the amine compound.

The values are determined by American Oil Chemists Society (A.O.C.S.) Official Method TF 2a - 64.

PREPARATION OF COMPOUNDS ACCORDING TO THE INVENTION

Example 1

To 1,150 g (2.03 mol; MW 566 g/mol) of dimer fatty acid D 96 were added 450 g (5.06 mol) of dimethylethanolamine and after addition of 2.3 g (0.2%) of hypophosphorous acid and 1.15 g (0.1%) of methanesulfonic acid the batch was heated to 180° C. under $N_2$. The water of reaction was gradually distilled off through a column. After the reaction ended (about 12 h), the excess dimethylethanolamine was distilled off in vacuo at 180° C. and 12 mbar.

| Analytical data: | |
| --- | --- |
| acid number | 2.8 |
| TOT | 148 |
| TERT | 147 |

Example 2

386 g (0.5 mol) of dimer fatty acid diester made in accordance with Example 1 was mixed with 150 g of isopropanol and quaternized with 147 g (1.17 mol) of dimethyl sulfate at 70° C. under $N_2$ until the TOT was less than 4.

| Analytical data: | |
|---|---|
| DS | 80% |
| TOT | 2.6 |
| Cat. $SO_3$ acid | 12.4 |
| pH (5%) | 6.9 |

Example 3

A solution of 465 g (0.61 mol) of dimer fatty acid diester made in accordance with Example 1 in 50 g of isopropanol was neutralized by the gradual dropwise addition of 121 g (1.2 mol) of lactic acid 90% at 50° C. by thorough stirring under $N_2$.

| Analytical data: | |
|---|---|
| DS | 82.8% |
| TOT | 108 |
| pH (5%) | 6.5 |

Example 4

A solution of 850 g (1.1 mol) of dimer fatty acid diester made in accordance with Example 1 in 110 g of isopropanol was quaternized at 60° C. under $N_2$ with 138 g (1.1 mol) of dimethyl sulfate. Then the mixture was neutralized by the gradual dropwise addition of 114 g (1.1 mol) of lactic acid 90% by thorough stirring under $N_2$.

| Analytical data: | |
|---|---|
| DS | 87% |
| TOT | 53 |
| Cat. $SO_3$ acid | 14.9 |
| pH (5%) | 6.3 |

Example 5

To 1,530 g (2.64 mol; MW 580 g/mol) of dimer fatty acid D 96 was added 3 g (0.2%) of hypophosphorous acid, followed by 650 g (6.4 mol) of dimethylaminopropylamine, and the batch was heated to 180° C. under $N_2$. The water of reaction was gradually distilled off through a column. After the reaction ended (about 4 h), the excess amine was distilled off in vacuo at 180° C. and 12 mbar.

| Analytical data: | |
|---|---|
| acid number | 0.7 |
| TOT | 157 |
| TERT | 156 |

Example 6

500 g (0.66 mol; MW 748 g/mol) of dimer fatty acid diamide made in accordance with Example 5 was admixed with 165 g of 1,2-propylene glycol and then quaternized under $N_2$ at 70° C. with 171 g (1.35 mol) of dimethyl sulfate until the TOT was less than 3.

| Analytical data: | |
|---|---|
| DS | 82.2% |
| TOT | 1.5 |
| Cat. $SO_3$ acid | 12.0 |
| pH (5%) | 7.2 |

Example 7

A solution of 810 g (1.1 mol) of dimer fatty acid diamide made in accordance with Example 5 in 250 g of 1,2-propylene glycol was quaternized at 60° C. with 143 g (1.1 mol) of dimethyl sulfate under $N_2$. The batch was then neutralized by the gradual dropwise addition of 113 g (1.1 mol) of lactic acid 90% by thorough stirring under $N_2$.

| Analytical data: | |
|---|---|
| DS | 79% |
| TOT | 47 |
| Cat. $SO_3$ acid | 13 |
| pH (5%) | 7.3 |

Example 8

A solution of 530 g (0.75 mol; MW 714 g/mol) of dimer fatty acid diamide made in accordance with Example 5 in 170 g of 1,2-propylene glycol was neutralized with 150 g (1.5 mol) of lactic acid 90% at 50° C. under $N_2$.

| Analytical data: | |
|---|---|
| DS | 71.2% |
| TOT | 95 |
| pH (5%) | 6.1 |

Example 9

To 540 g (0.75 mol; MW 725 g/mol) of dimer fatty acid diester made in accordance with Example 1 was gradually added dropwise at 180° C. under $N_2$ 76.5 g (0.75 mol) of dimethylaminopropylamine in the course of 2 h. After a further 4 h the liberated dimethylethanolamine was distilled off in vacuo at 12 mbar and 180° C.

| Analytical data: | |
|---|---|
| AN | 2.0 |
| TOT | 151 |

Example 10

740 g (1.0 mol; MW 740 g/mol) of dimer fatty acid ester-amide made in accordance with Example 9 was admixed with 170 g of isopropanol and then quaternized under $N_2$ at 70° C. with 249 g (1.94 mol) of dimethyl sulfate.

| Analytical data: | |
|---|---|
| DS | 85% |
| TOT | 1.8 |
| Cat. $SO_3$ | 13.2 |

-continued

| Analytical data: | |
|---|---|
| pH (5%) | 6.6 |

Example 11

A solution of 740 g (1 mol) of dimer fatty acid esteramide made in accordance with Example 9 in 80 g of isopropanol was neutralized by the gradual dropwise addition of 200 g (2 mol) of lactic acid 90% at 50° C. by thorough stirring under $N_2$.

| Analytical data: | |
|---|---|
| DS | 85.2% |
| TOT | 112 |
| pH (5%) | 5.3 |

Example 12

A solution of 740 g (1 mol) of dimer fatty acid esteramide made in accordance with Example 9 in 160 g of isopropanol was quaternized at 60° C. with 126 g (1 mol) of dimethyl sulfate under $N_2$. Then the mixture was neutralized by the gradual dropwise addition of 100 g (1 mol) of lactic acid 90% by thorough stirring under $N_2$.

| Analytical data: | |
|---|---|
| DS | 83% |
| TOT | 50 |
| Cat. $SO_3$ acid | 13.3 |

Application Testing

Application testing was carried out according to the test methods customary in this field as follows:

Preparation of Final-Rinse Fabric Softener

The examples listed below in the table were prepared as follows:

To tap water of 9° German hardness at 20° C. were added with thorough stirring 0.625 g of SANDOLAN® milling blue NBL-150 1% (from Sandoz), 0.250 g of DOW antifoam DB-110A (from DOW Chemicals), and then the amount specified in the examples of substance according to the present invention was dissolved therein. Thereafter the batch was adjusted if necessary to pH about 3 with HCl in the case of the quaternary compounds and with lactic acid in the case of the salts.

Verification of Remoisture Capability and Soft Hand

| Test fabric: | standard milling terry fabric 100% cotton |
|---|---|
| size: | 80 × 50 cm from Möwe, Reutlingen |

3 kg of the test fabric were washed 2 times with 100 g each time of detergent (test detergent from WFK-Testgewebe GmbH Krefeld) and then twice without detergent (each time by the 95° C. wash program without prewash).

The test fabrics dried at room temperature were then dipped into the fabric softener solution containing 0.025% by weight of compound according to the present invention or of commercial fabric softener in tap water of 9° German hardness 15°–20° C. for 10 min.

The fabrics dried at room temperature were rated by 9 test persons in respect of their softness. They were assigned ratings on a scale from 0 to 5, where 0 means harsh and 5 means very soft (=good). The final assessment is the arithmetic average.

The remoisture capability was measured in accordance with German Standard Specification DIN 53 924, except that the strips of the test pieces were 1.5 cm in width.

| | Final-rinse fabric softener | | | | |
|---|---|---|---|---|---|
| | Component according to the invention | | | | |
| Example | as per Example | Amount per 100 g of total mixture | Assessment | Remoisture capability | Soft hand |
| 1 | 2 | 31 g | clear solution of low viscosity | 100% | good |
| 2 | 2 | 6.3 g | clear solution of low viscosity | 100% | good |
| 3 | 4 | 30.5 g | clear solution of low viscosity | 100% | good |
| 4 | 4 | 6 g | clear solution of low viscosity | 100% | good |
| 5 | 3 | 24.2 g | clear solution of low viscosity | 100% | good |
| 6 | 6 | 31 g | clear solution of low viscosity | 97% | good |
| 7 | 6 | 6 g | clear solution of low viscosity | 97% | good |
| 8 | 7 | 38 g | clear solution of low viscosity | 98% | good |
| 9 | 7 | 18.8 g | clear solution of low viscosity | 98% | good |
| 10 | 8 | 35.1 g | clear solution of low viscosity | 97% | good |
| 11 | 8 | 7 g | clear solution of low viscosity | 97% | good |
| 12[a] | 10 | 29.3 g | clear solution | 97% | good |
| 13[a] | 10 | 6 g | clear solution of low viscosity | 97% | good |
| 14 | 12 | 28.5 g | clear solution of low viscosity | 100% | good |
| 15 | 12 | 5.7 g | clear solution of low viscosity | 100% | good |
| 16 | 11 | 28.4 g | clear solution of low viscosity | 99% | good |
| 17 | 11 | 5.7 g | clear solution of low viscosity | 99% | good |
| 18 | 2 | 37.1 g | clear solution of low viscosity | 100% | good |
| 19 | 6 | 37.1 g | clear solution of low viscosity | 97% | good |
| 20 | 7 | (30%) | clear, thin solution | 98% | good |
| Comparative experiments | | | | | |
| 1 | Comparison[b] | 18.8 g | dispersion | 77% | good |
| 2 | Comparison[b] | 25.1 g | dispersion | 77% | good |
| 3 | Comparison[c] | 6.7 g | dispersion | 64% | very good |
| 4 | — | — | — | 100% | satisfactory |

[a] component according to the invention preheated to 50° C. and incorporated at a water temperature of 40° C.
[b] comparative experiment: commercially available quaternary ammonium compound (3-alkoxyloxy-2-hydroxypropyl)-trimethylammonium chloride
[c] REWOQUAT ® W 90: quaternary imidazolinium derivative from REWO Chemische Werke, Steinau an der Straße.

The compounds according to the present invention can also be used with success in cosmetic formulations: in the hair care sector, depending on the formulation, not only for cleaning, i.e. as shampoo, but also for conditioning the hair to improve the combability.

Used in shampoos, they have the considerable advantage over conventional cationic compounds that they give clear solutions in water even in the presence of anionic surfactants, whereas prior art products give only dispersions. The advantage of solutions over dispersions in respect of storage life over a wide temperature range is known.

A further advantage is that the simultaneous presence of anionic and cationic compounds in a formulation makes this formulation useful not only in cleaning but also in conditioning.

In addition, these formulations accord with the modern view of a multipurpose agent, since they have a cleaning and conditioning effect not only on the hair but also on the skin. By using the compounds according to the present invention it is thus possible to meet the consumer's demand for body-hair care shampoos without problem.

The cosmetic formulations may additionally include the customary cosmetic surfactants, scents, preservatives, dyes, plant extracts or other cosmetic additives.

Suitable surfactants, besides the known betaines, amphoteric and nonionic compounds, include for the cleaning formulation in particular anionic surfactants such as carboxylates, alkyl sulfates, alkyl ether sulfates, alkyl sulfonates, alkyl ether sulfonates, alkyl sulfosuccinates. According to the invention preference is given to alkylamidobetaines such as REWOTERIC® [1] AM B 13 and AM B 14, carboxyglycinates such as REWOTERIC® AM 2 C NM, carboxypropionates such as REWOTERIC® AM KSF 40, sulfobetaines such as REWOTERIC® AM CAS, anionic surfactants such as ether sulfate REWOPOL® [2] NL 3, ether carboxylates such as REWOPOL® CLN 100, sulfosuccinates such as REWOPOL® SB FA 30, REWOPOL® SBZ, REWODERM® [3] SPS, nonionic surfactants such as glycerol fatty acid ester ethoxylates such as REWODERM® ES 90, glycerol monostearate such as REWOMUL® [4] MG, cetyl alcohol ([1], [2], [3], and [4] are trademarks of REWO Chemische Werke GmbH, Steinau an der StraBe).

The compounds according to the present invention can be used in amounts of 0.5-10 parts by weight, preferably 1-8 parts by weight, and more preferably 1-3 parts by weight, in the case of shampoos, and 1-7 parts by weight, preferably 1-5 parts by weight, in the case of rinses and conditioners. In addition to these components, the other surfactants are customarily used in amounts of 1-20 parts by weight, preferably 5-15 parts by weight, in shampoos and in amounts of 0.1-10 parts by weight, preferably 1-5 parts by weight, in rinses and conditioners.

The thickeners used are present in amounts sufficient to provide effective thickening, typically 1-8 parts by weight of the customary compounds such as glycerol fatty acid ester ethoxylates, fatty alcohol ethoxylates, fatty acid alkylolamides and the customary alkali metal, alkaline earth metal and ammonium salts which are soluble in water in amounts of at least 1% by weight at 20° C. Preferred examples of such salts are NaCl and $NH_4Cl$.

Cosmetic Formulations

The following shampoos for body and hair can be produced by simply mixing the ingredients in water.

| Formulation No. 1: Conditioning shampoo |
|---|
| 50 parts of REWOPOL® NL 3-28[1] |
| 10 parts of REWOTERIC® AM KSF 40[2] |
| 2 parts of REWOMINOX® B 204[3] |
| 20 parts of Examples 6 and 10 according to the invention |
| 0.3 part of citric acid |
| 3.0 parts of sodium chloride |
| ad 100 parts demineralized water |

® trademark of REWO Chem. Werke GmbH
[1] sodium lauryl ether sulfate
[2] amphoteric surfactant, salt-free
[3] alkylamidopropyldimethylamine oxide

| Formulation No. 2: Conditioning shampoo |
|---|
| 50 parts of REWOPOL® NL 3-28[1] |
| 10 parts of REWOPOL® SB FA 30[4] |
| 2 parts of REWOMINOX® B 204[3] |
| 1.3 parts of Examples 6 and 10 according to the invention |
| 0.1 part of citric acid |
| 4.0 parts of sodium chloride |
| ad 100 parts demineralized water |

[4] fatty alcohol polyglycol ether sulfosuccinate

| Formulation No. 3: Shower and hair shampoo with conditioning effect |
|---|
| 1.5 parts of Example 2 according to the invention |
| 2 parts of REWODERM® ES 90[6] |
| 2 parts of REWODERM® LIS 75[10] |
| 10 parts of REWOTERIC® AM B 13[11] |
| 25 parts of REWOPOL® NL 3-28[1] |
| 8 parts of REWOPOL® SBZ[12] |
| ad 100 parts demineralized water |

[10] fatty acid monoglyceride polyglycol ether, modif.
[11] alkylamidobetaine
[12] fatty acid polyglycol ester sulfosuccinate.

All the formulations were examined in respect of improvement in the ease of combing the hair and recipe 6 additionally in respect of the skin smoothness feel after showering. The tests were carried out by 10 experienced examiners, the final report result being the statistical average.

The ease of combing was rated for all the formulations as good with reduced comb resistance. The average values achieved on the scale from 1 to 7 were 4-7.

The feeling on the skin in the case of formulation 3 was assessed as creamily soft in the case of wet skin and as smoothly soft in the case of dry skin.

The following formulations were prepared as follows:

| Formulation No. 4: Hair rinse, preparable cold |
|---|
| 1.0 part of NATROSOL®[1] 250 HHR[7] |
| 1.0 part of REWOQUAT® RTM 50[5] |
| 2.0 parts of Examples 6 and 10 according to the invention |
| 1.0 part of REWODERM® ES 90[6] |
| 0.4 part of citric acid |
| ad 100 parts demineralized water |

[5] ricinoleic acid propylamidotrimethylammonium methosulfate
[6] fatty acid monoglyceride polyglycol ether
[7] hydroxyethylcellulose
®[1] registered trademark of Aqualon

| Formulation No. 5: Hair conditioner | |
|---|---|
| Phase A: | 5.5 parts of Examples 6 and 10 according to the invention |
| | 1.5 parts of cetyl alcohol |
| | 3.0 parts of REWOMUL® MG[9] |
| Phase B: | 2.0 parts of REWODERM® ES 90[6] |
| | 2.0 parts of REWOPOL® SB FA 30[4] |
| | 0.2 part of citric acid |

|  |
|---|
| 85.8 parts demineralized water |

8) glycerol monostearate

Formulation No. 6: Hair rinse

Phase A: 3.0 parts of Example 10 according to the invention
1.0 part of cetyl alcohol
1.0 part of TEGINACID ® 2) 9)
Phase B: 0.2 part of citric acid
ad 100 parts demineralized water ®2)registered trademark of Goldschmidt
9)glycerol monostearate, acid-stable.

The hair rinse of formulation 4 is produced by preswelling NATROSOL® 250 HHR in demineralized water at room temperature and then adding the remaining components with intensive stirring. A clear solution of medium viscosity with a long storage life is obtained.

The hair rinse of formulation 6 and the hair conditioner of formulation 5 were prepared by preparing two phases A) and B) separately in advance by respectively mixing with heating to 65° C. and simultaneous thorough stirring, and then subsequently dispersing phase A) in phase B).

These formulations were examined in respect of wet and dry combability as specified above.

Not only the wet but also the dry combability scored the maximum attainable 10 points with the majority of testers. The statistical average was 8.

| Evaluation scale: | |
|---|---|
| 1–3 | difficult to comb |
| 4–7 | readily combable, hardly any resistance to comb |
| 8–10 | very readily combable, even less resistance to combing. |

What is claimed is:

1. An aqueous final-rinse fabric softener comprising 5 to 30% by weight of at least one ammonium compound of the general formula (1)

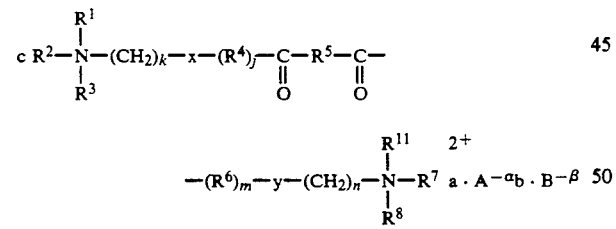

wherein
$R^1$ and $R^{11}$ are the same or different and each is H, $-CH_3$, $-C_2H_5$, $-(C_3H_6O)_pH$, or $-(C_2H_4O)_eH$;
$R^2$, $R^3$, $R^7$ and $R^8$ are the same or different and each is a straight-chain or branched alkyl radical containing 1–18 carbon atoms, or a straight-chain or branched alkylene radical containing 2–18 carbon atoms;
$R^4$ and $R^6$ are the same or different and are represented by the formula $-(CH_2-CHR^9-O)_d-$ wherein d is zero to 20 and in each of the units of the formula $-(CH_2-CHR^9-O)-$ $R^9$ is independently H or $-CH_3$, and wherein the oxygens of said alkoxy groups are attached to the carboxyl groups in formula (1), provided that $R^9$ is $-H$ in up to 10 of said units and $R^9$ is $-CH_3$ in up to 10 of said units;

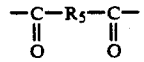

is the radical of a dimerized fatty acid, said fatty acid containing 16–22 carbon atoms before dimerization;
x and y are independently $-O-$ or $-NH-$;
$A^{-\alpha}$ and $B^{-\beta}$ are the same or different and each is the anion of a water-soluble monobasic or polybasic inorganic or organic acid, and a, b and c are integers related such that $c = [(a)(\alpha) + (b)(\beta)]/2$;
k and n are the same or different and each is an integer from 2–4;
p and e are the same or different and each is an integer from 1–5; and
j and m are the same or different and each is zero or one, provided that j is zero when x is $-NH-$ and m is zero when y is $-NH-$.

2. A conditioner in accordance with claim 1, further comprising one or more components selected from the group consisting of water, dyes, perfume, thickeners and customary auxiliary and additive substances.

3. An aqueous final-rinse fabric conditioner as claimed in claim 1, wherein in the general formula (1) $R^1$ and $R^{11}$ are the same or different and each is H or $-CH_3$;
$R^2$, $R^3$, $R^7$ and $R^8$ are methyl;
$R^5$ is the radical of a dimerized fatty acid having a dimer content of at least about 80% by weight;
k and n are each 2 or 3;
j and m are zero; and
$A^{-\alpha}$ and $B^{-\beta}$ are the same or different and each is lactate or methylsulfate; said at least one compound of formula (1) being formed from one or more dimeric acids of the formula HOOC—R$^5$—COOH formed by dimerization of fatty acids, wherein said one or more dimeric fatty acids comprise at least about 80% by weight of all products of said dimerization present in said conditioner.

4. An aqueous hair cleaning and conditioning composition comprising
a) 0.5–10 parts by weight of at least one of the ammonium compounds of the general formula (1)

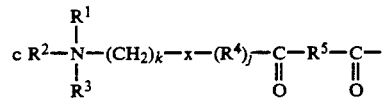

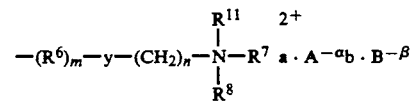

wherein
$R^1$ and $R^{11}$ are the same or different and each is H, $-CH_3$, $-C_2H_5$, $-(C_3H_6O)_pH$, or $-(C_2H_4O)_eH$;
$R^2$, $R^3$, $R^7$ and $R^8$ are the same or different and each is a straight-chain or branched alkyl radical containing 1–18 carbon atoms, or a straight-chain or branched alkylene radical containing 2–18 carbon atoms;

R[4] and R[6] are the same or different and are represented by the formula $-(CH_2-CHR^9-O)_d-$ wherein d is zero to 20 and in each of the units of the formula $-(CH_2-CHR^9-O)-$ R[9] is independently H or $-CH_3$, and wherein the oxygens of said alkoxy groups are attached to the carboxyl groups in formula (1), provided that R[9] is $-H$ in up to 10 of said units and R[9] is $-CH_3$ in up to 10 of said units;

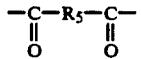

is the radical of a dimerized fatty acid, said fatty acid containing 16-22 carbon atoms before dimerization, x and y are independently $-O-$ or $-NH-$;

$A^{-\alpha}$ and $B^{-\beta}$ are the same or different and each is the anion of a water-soluble monobasic or polybasic inorganic or organic acid, and a, b and c are integers related such that $c=[(a)(\alpha)+(b)(\beta)]/2$;

k and n are the same or different and each is an integer from 2-4;

p and e are the same or different and each is an integer from 1-5; and j and m are the same of different and each is zero or one, provided that j is zero when x is $-NH-$ and m is zero when y is $-NH-$;

b) 1.0-20 parts by weight of at least one nonionic, amphoteric, zwitterionic, or ionic surfactant;

c) 0.1-10 parts by weight of one or more components selected from the group consisting of thickeners, scents, preservatives, dyes, plant extracts and other additive and auxiliary substances; and d) ad 100 water.

5. An aqueous shower and hair shampoo composition comprising a) 0.5-10 parts by weight of one or more ammonium compounds of the general formula (1)

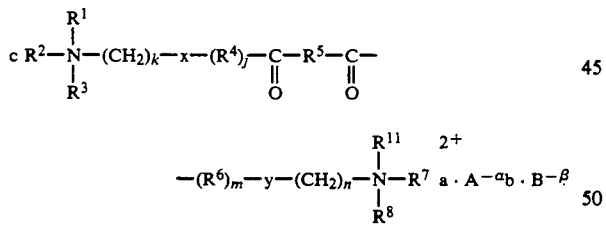

wherein

R[1] and R[11] are the same or different and each is H, $-CH_3$, $-C_2H_5$, $-(C_3H_6O)_pH$, or $-(C_2H_4O)_eH$;

R[2], R[3], R[7] and R[8] are the same or different and each is a straight-chain or branched alkyl radical containing 1-18 carbon atoms, or a straight-chain or branched alkylene radical containing 2-18 carbon atoms;

R[4] and R[6] are the same or different and are represented by the formula $-(CH_2-CHR^9-O)_d-$ wherein d is zero to 20 and in each of the units of the formula $-(CH_2-CHR^9-O)-$ R[9] is independently H or $-CH_3$, and wherein the oxygens of said alkoxy groups are attached to the carboxyl groups in formula (1), provided that R[9] is $-H$ in up to 10 of said units and R[9] is $-CH_3$ in up to 10 of said units;

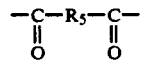

is the radical of a dimerized fatty acid, said fatty acid containing 16-22 carbon atoms before dimerization;

x and y are independently $-O-$ or $-NH-$;

$A^{-\alpha}$ and $B^{-\beta}$ are the same or different and each is the anion of a water-soluble monobasic or polybasic inorganic or organic acid, and a, b and c are integers related such that $c=[(a)(\alpha)+(b)(\beta)]/2$;

k and n are the same or different and each is an integer from 2-4;

p and e are the same or different and each is an integer from 1-5; and j and m are the same or different and each is zero or one, provided that j is zero when x is $-NH-$ and m is zero when y is $-N-$, said one or more ammonium compounds being formed from one or more dimeric fatty acids of the formula $HOOC-R^5-COOH$ formed by dimerization fatty acids, wherein said one or more dimeric fatty acids comprise at least about 80% by weight of all products of said dimerization present in said composition;

k and n are the same or different and each is 2 or 3;

j and m are both zero; and $A^{-\alpha}$ and $B^{-\beta}$ are the same or different and each is the lactate or methylsulfate;

b) 1.0-10 parts by weight of at least one nonionic, amphoteric, zwitterionic, or ionic surfactant;

c) 0.1-5 parts by weight of one or more components selected from the group consisting of thickeners, scents, preservatives, dyes, plant extracts and other additive and auxiliary substances; and d) ad 100 water.

6. An aqueous hair conditioning composition comprising a) 1-7 parts by weight of one or more ammonium compounds of the general formula (1)

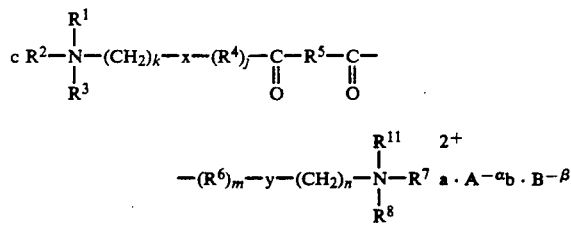

wherein

R[1] and R[11] are the same or different and each is H, $-CH_3$, $-C_2H_5$, $-(C_3H_6O)_pH$, or $-(C_2H_4O)_eH$;

R[2], R[3], R[7] and R[8] are the same or different and each is a straight-chain or branched alkyl radical containing 1-18 carbon atoms, or a straight-chain or branched alkylene radical containing 2-18 carbon atoms;

R[4] and R[6] are the same or different and are represented by the formula $-(CH_2-CHR^9-O)_d-$ wherein d is zero to 20 and in each of the units of the formula $-(CH_2-CHR^9-O)-$ R[9] is independently H or —$CH_3$, and wherein the oxygens of said alkoxy groups are attached to the carboxyl groups in formula (1), provided that $R^9$ is —H in up to 10 of said units and $R^9$ is —$CH_3$ in up to 10 of said units;

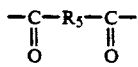

is the radical of a dimerized fatty acid, said fatty acid containing 16-22 carbon atoms before dimerization;

x and y are independently —O— or —NH—;

$A^{-\alpha}$ and $B^{-\beta}$ are the same or different and each is the anion of a water-soluble monobasic or polybasic inorganic or organic acid, and a, b and c are integers related such that $c=[(a)(\alpha)+(b)(\beta)]/2$;

k and n are the same or different and each is an integer from 2-4;

p and e are the same or different and each is an integer from 1-5; and j and m are the same or different and each is zero or one, provided that j is zero when x is —NH— and m is zero when y is —NH—, said one or more ammonium compounds being formed from one or more dimeric fatty acids of the formula HOOC—$R^5$—COOH formed by dimerization of fatty acids, wherein said one or more dimeric fatty acids comprise at least about 80% by weight of all products of said dimerization present in said composition;

k and n are the same or different and each is 2 or 3;

j and m are both zero; and $A^{-\alpha}$ and $B^{-\beta}$ are the same or different and each is lactate or methylsulfate;

b) 1.0-20 parts by weight of at least one nonionic, amphoteric, zwitterionic, or ionic surfactant;

c) 0.1-5 parts by weight of one or more components selected from the group consisting of thickeners, scents, preservatives, dyes, plant extracts and other additive and auxiliary substances; and d) ad 100 water.

* * * * *